United States Patent
Park et al.

(10) Patent No.: US 7,579,294 B2
(45) Date of Patent: Aug. 25, 2009

(54) SYNTHESIS OF SUPPORTED TRANSITION METAL CATALYSTS

(75) Inventors: Jaiwook Park, Pohang-si (KR); Namdu Kim, Pohang-si (KR); Min Serk Kwon, Pohang-si (KR); Cheon Min Park, Pohang-si (KR)

(73) Assignee: Postech Foundation (KR)

( * ) Notice: Subject to any disclaimer, the term of this patent is extended or adjusted under 35 U.S.C. 154(b) by 308 days.

(21) Appl. No.: 11/718,017

(22) PCT Filed: Feb. 2, 2005

(86) PCT No.: PCT/KR2005/000307

§ 371 (c)(1), (2), (4) Date: Apr. 26, 2007

(87) PCT Pub. No.: WO2006/070964

PCT Pub. Date: Jul. 6, 2006

(65) Prior Publication Data

US 2009/0137385 A1    May 28, 2009

(30) Foreign Application Priority Data

Dec. 29, 2004   (KR) .................. 10-2004-0114826

(51) Int. Cl.
*B01J 31/02* (2006.01)
*B01J 31/06* (2006.01)

(52) U.S. Cl. .............. 502/150; 502/152; 502/154; 502/155; 502/159; 502/162; 502/166; 502/171

(58) Field of Classification Search .......... 502/150, 502/152, 154, 155, 162, 166, 171, 159
See application file for complete search history.

(56) References Cited

U.S. PATENT DOCUMENTS 6,169,192 B1 * 1/2001 Pugin et al. ............. 556/11

OTHER PUBLICATIONS

Namdu Kim, et al., One-pot synthesis of recyclable palladium catalysts for hydrogenations and carbon-carbon coupling reactions, Tetrahedron Letters 45 ( )2004) 7057-7059.

* cited by examiner

Primary Examiner—Elizabeth D Wood
(74) Attorney, Agent, or Firm—Baker & Hostetler, LLP (57) ABSTRACT

A highly active and recyclable supported transition metal catalyst can be prepared by a simple process comprising mixing with heating a transition metal complex, a metal-chelating agent and an alkoxide of Ti, Al or Si, followed by treatment with water to induce a sol-gel reaction among the reactants.

13 Claims, 5 Drawing Sheets

SYNTHESIS OF SUPPORTED TRANSITION METAL CATALYSTS

FIELD OF THE INVENTION

The present invention relates to a simple method for preparing highly active and recyclable supported transition metal catalysts.

BACKGROUND OF THE INVENTION

Transition metal catalysts such as palladium and titanium catalysts are extensively used in various industrial processes including the hydrogenation of alkenes and alkynes, the oxidation of alcohols, the olefination of alkyl halides, and carbon-carbon coupling reactions.

Homogeneous transition metal catalysts are difficult to separate for reuse, and therefore, there have been various attempts to develop recyclable transition metal catalysts, e.g., heterogeneous palladium catalysts obtained by immobilizing palladium moieties onto inorganic supports or organic polymers; palladium nanoparticles; colloidal palladium species; and polymer-incarcerated palladiums ([Djakovitch, L. et al., *J. Am. Chem. Soc.* 2001, 123, 5990; Kim, S.-W. et al., *J. Am. Chem. Soc.* 2002, 124, 7642; Roucoux, A. et al. *Chem. Rev.* 2002, 102, 3757; and Akiyama, R. et al., *J. Am. Chem. Soc.* 2003, 125, 3412]).

The conventional recyclable catalysts, however, suffer from the problems of low reactivity, deactivation, leaching of the metal component and complicated synthetic procedures.

SUMMARY OF THE INVENTION

Accordingly, it is an object of the present invention to provide a simple method for preparing a highly active and recyclable supported transition metal catalyst.

In accordance with one aspect of the present invention, there is provided a method for preparing a supported transition metal catalyst, which comprises mixing with heating an organic transition metal complex, a metal-chelating agent and an alkoxide of a metal selected from the group consisting of Ti, Al and Si, and adding water thereto to induce a sol-gel reaction.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The method of the present invention is characterized by heat-mixing readily available three components, i.e., an organic transition metal complex, a metal-chelating agent and an alkoxide of Ti, Al or Si, followed by treatment with water to form transition metal nanoparticles supported on a carrier in one pot.

In accordance with the method of the present invention, first, an organic transition metal complex, a metal-chelating agent and an alkoxide of Ti, Al or Si are mixed and heated at a temperature ranging from 50 to 200° C., preferably 100 to 150° C., for 2 to 20 hrs to form nano-sized transition metal particles. Then, water is added to the resulting suspension and heated to allow a sol-gel reaction to take place at a temperature ranging from 50 to 200° C., preferably 100 to 130° C., for 1 to 20 hrs, to provide a carrier-supported transition metal (transition metal/carrier) catalyst.

The organic transition metal complex used in the present invention may comprise at least one transition metal selected from the group consisting of Pd, Pt, Ru, Ni, Ir, Co, Rh, Os, Sm, Fe, Sc, Se, Re, Au and Ag, and one or more anionic ligands such as hydride (H—), chloride (Cl—), cyanide (CN—) and acetyl($CH_3COO$—), or one or more neutral ligands such as triphenylphosphine ($P(C_6H_5)_3$), dibenzylidene acetone ($C_6H_5CH{=}CHCOCH{=}CHC_6H_5$), carbonyl (CO) and diene.

Representative examples of the organopalladium complex which may be used in the present invention include tetrakistriphenylphosphine palladium(0) ($Pd[P(C_6H_5)_3]_4$), palladium(II) acetate ($Pd(OAc)_2$), palladium(II) chloride, trisdibenzylidene acetone dipalladium(0) (($C_6H_5CH{=}CHCOCH{=}CHC_6H_5)_3Pd_2$), trisdibenzylidene acetone dipalladium(0) chloroform adduct (($C_6H_5CH{=}CHCOCH{=}CHC_6H_5)_3{\cdot}Pd_2CHCl_3$), bis[1,2-bis(diphenylphosphino)ethane]palladium(0) ($Pd[(C_6H_5)_2PCH_2CH_2P(C_6H_5)_2]_2$), bis(tri-t-butylphosphino)palladium(0) ($Pd[P(C_4H_9)_3]_2$) and bis(tricyclohexylphosphino)palladium(0) ($Pd[P(C_6H_{11})_3]_2$), wherein tetrakistriphenylphosphine palladium(0) is preferred.

The metal-chelating agent used in the present invention which acts to help the formation of nano-sized transition metal particles from the transition metal complex may be a polyethylene glycol having 1 to 30 ethylene repeating units (its structure: H—($OCH_2CH_2$)$_n$—OH, wherein n is an integer of 1 to 30) or an alcohol having 1 to 10 carbon atoms. The ethylene glycol multipolymer is preferably triethylene glycol or tetraethylene glycol, and the alcohol is preferably a CT-4 alcohol. The metal-chelating agent may be employed in an amount ranging from 1 to 500 mol, preferably 5 to 50 mol based on 1 mol of the transition metal complex.

The alkoxide of Ti, Al or Si used in the present invention may be tetraalkyl orthosilicate ($Si(OR)_4$), titanium(IV) tetraalkoxide ($Ti(OR)_4$) or aluminum(III) trialkoxide ($Al(OR)_3$), wherein R is $C_{1-10}$ alkyl, preferably $C_{1-4}$ alkyl. The metal alkoxide compound may be employed in an amount ranging from 10 to 1000 mol, preferably 150 to 300 mol based on 1 mol of the transition metal complex.

The water for a sol-gel reaction may be employed in an amount ranging from 1 to 100 mol, preferably 2 to 10 mol based on 1 mol of the metal alkoxide compound.

Then, the sol-gel reaction product is filtered, washed with an appropriate solvent and dried to obtain a heterogeneous, carrier-supported transition metal catalyst. The suitable solvent for washing the product may be acetone, tetrahydrofuran, ethylacetate, diethylether, 1,4-dioxane, benzene, toluene, N,N-dimethylformamide, dimethylsulfoxide, methanol, ethanol, n-propanol, i-propanol, dichloromethane and chloroform, acetone and tetrahydrofuran being preferred.

The carrier-supported transition metal catalyst prepared by the inventive method has 1 to 10 nm-sized transition metal particles uniformly dispersed on the carrier which consists mainly of titania, alumina or silica having a large quantity of hydroxy groups and may comprise a part of the used metal-chelating agent. The small size and uniform dispersion of the transition metal nanoparticles results in a large specific surface area of the active metal.

As described above, in accordance with the method of the present invention, a recyclable supported transition metal catalyst which has a high activity and keeps its original activity even after repeated use of over 10 recycles can be easily synthesized in one pot. The inventive catalyst can be advantageously employed in the hydrogenation of alkenes and alkynes, the oxidation of alcohols, carbon-carbon coupling reactions and the like.

The following Examples are given for the purpose of illustration only, and are not intended to limit the scope of the invention.

<Preparation of Supported Palladium Catalysts>

EXAMPLE 1

0.42 g (2.20 mmol) of tertraethylene glycol, 0.25 g (0.22 mmol) of tetrakistriphenylphosphine palladium(0), 9.5 g (38.5 mmol) of aluminum tri-sec-butoxide and 3 mL (32.7 mmol) of butanol were mixed in a 25 mL reaction vessel and kept at 120° C. for 10 hours. Then, 1.80 mL of water was added thereto, the mixture was kept at the same temperature for 0.5 hours, and then cooled to room temperature. The precipitated solids were filtered, washed three times with 10 mL of acetone and dried for 24 hrs to obtain 2.75 g of a palladium catalyst supported on an alumina-based carrier (palladium particle average-size: 3 nm, palladium content: 0.85%, palladium yield: 98.0%).

Figure 1A:
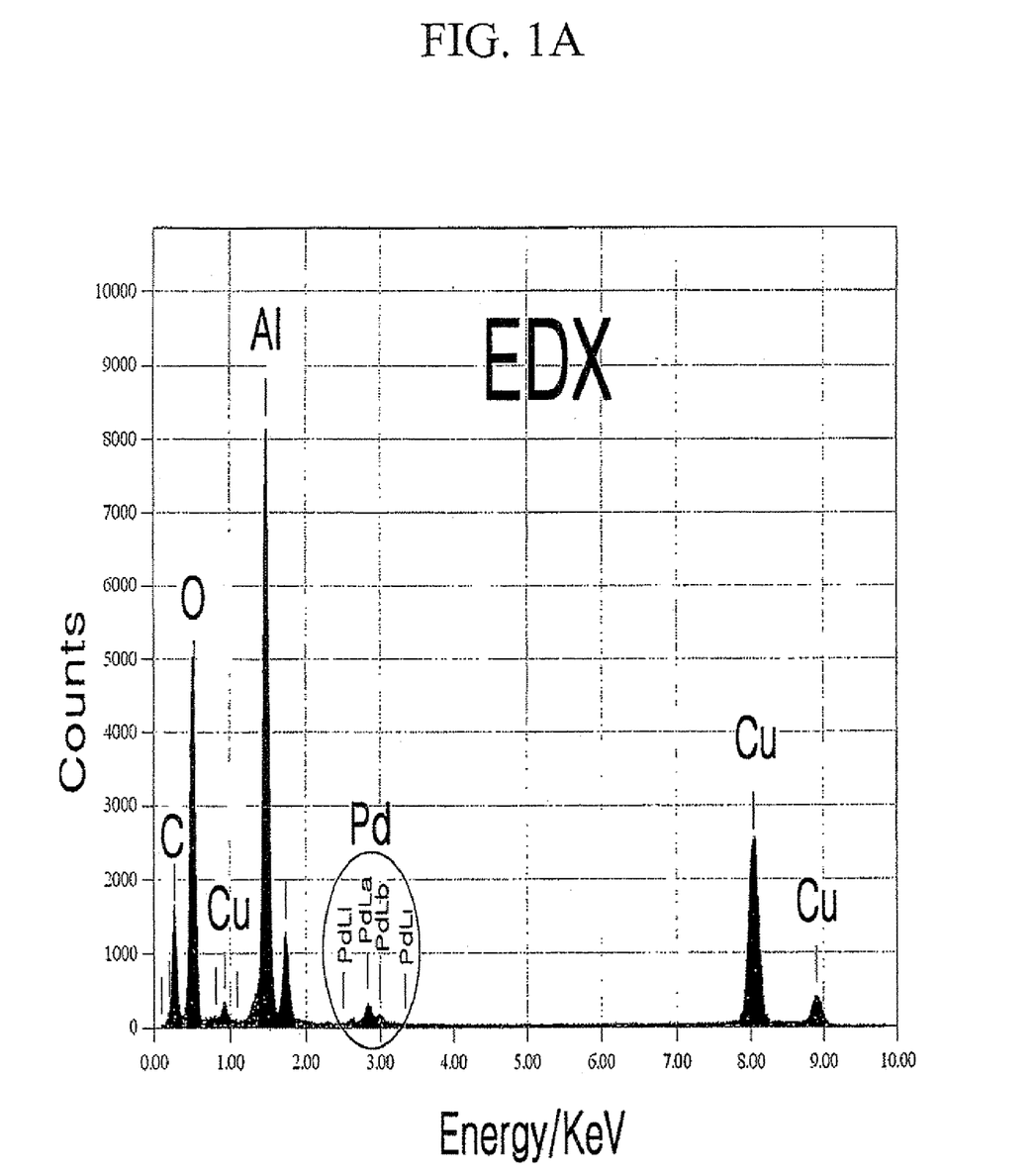
FIG. 1A: An energy dispersive x-ray (EDX) scan of the palladium catalyst prepared in Example 1.
Figure 1B:
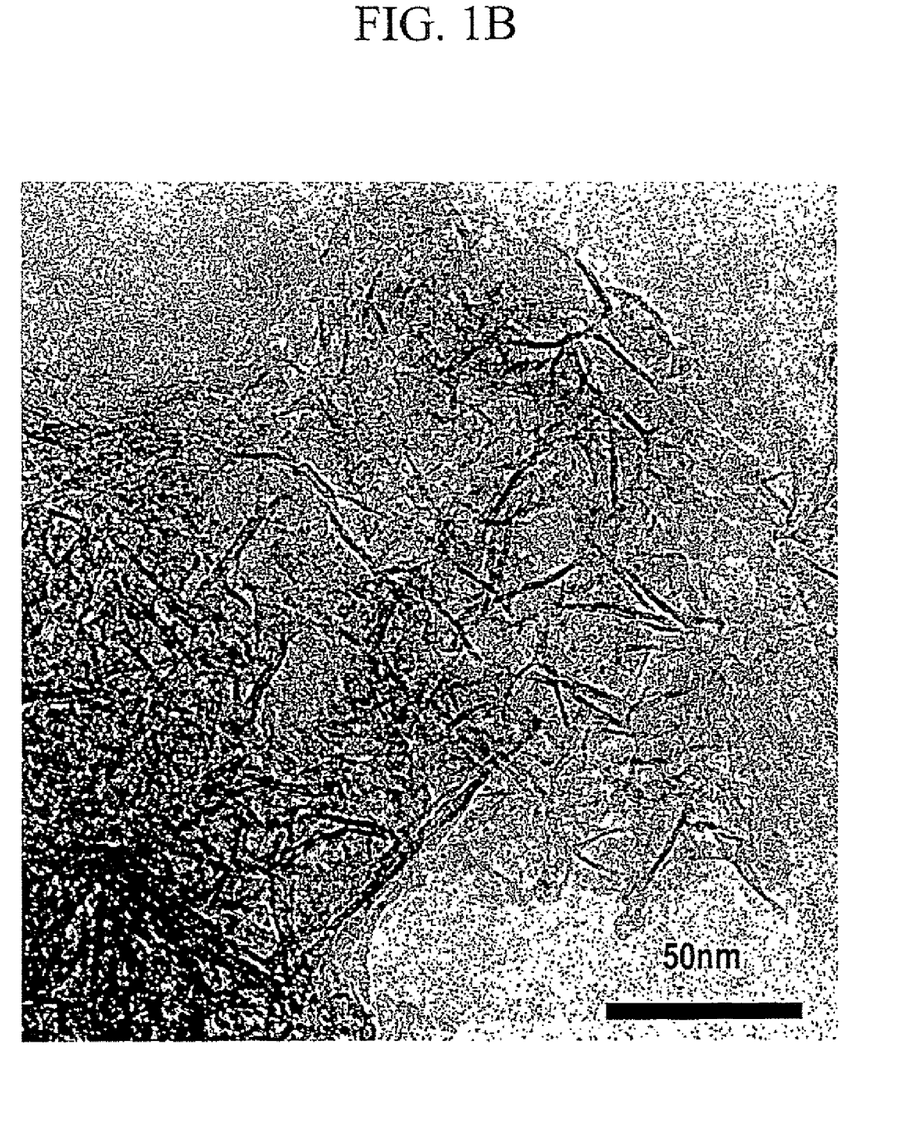
FIGS. 1B and 1C: Transmission electron microscope (TEM) photographs of the palladium catalyst prepared in Example 1.
Figure 1C:
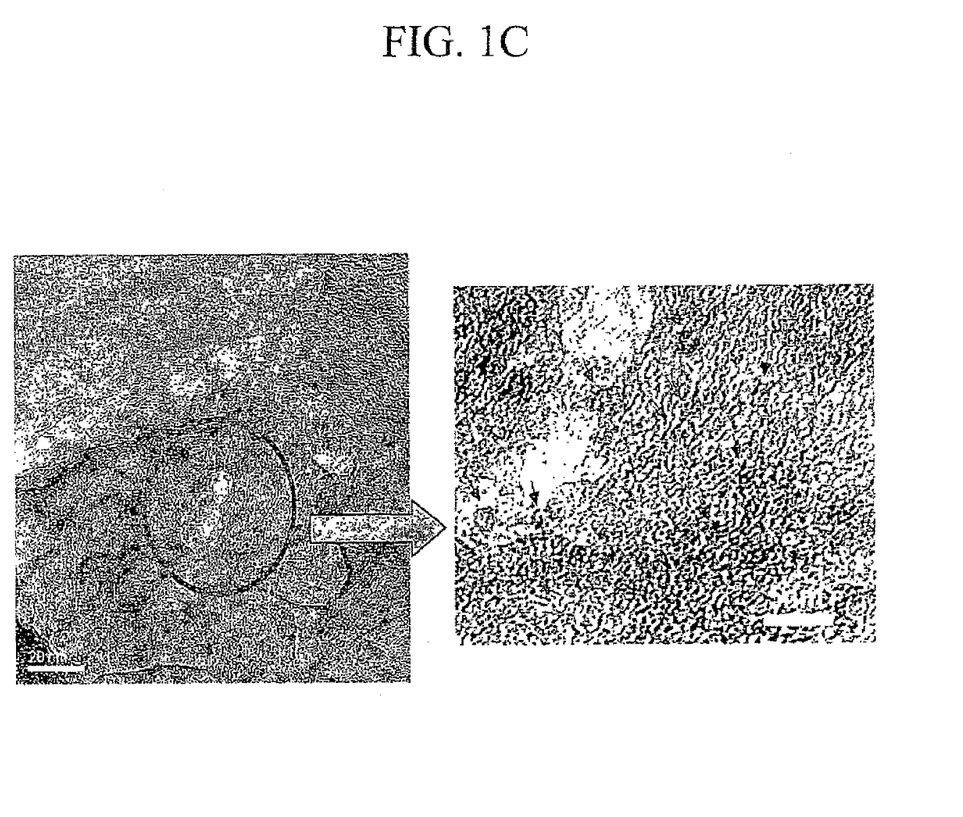

An energy dispersive x-ray (EDX) scan of the supported palladium catalyst thus obtained is shown in FIG. 1A which confirms the presence of palladium particles. Lower and higher magnification transmission electron microscope (TEM) photographs thereof are shown in FIGS. 1B and 1C, respectively.

The results of $N_2$-absorption BET analysis at 77K and CO-chemisorption at room temperature show that the supported palladium catalyst of Example 1 has a specific surface area of 611.5 $m^2$/g catalyst, a palladium surface area of 216.53 $m^2$/g catalyst and a palladium dispersion of 48%.

EXAMPLE 2

0.190 g (1.00 mmol) of tertraethylene glycol, 0.116 g (0.100 mmol) of tetrakistriphenylphosphine palladium(0) and 2.58 g (17.0 mmol) of tetramethyl orthosilicate were mixed in a 25 mL reaction vessel and kept at 120° C. for 2 hours. Then, 0.920 mL of water was added thereto, the mixture was kept at the same temperature for 10 hours, and then cooled to room temperature. The precipitated solids were filtered, washed tree times with 10 mL of acetone and dried for 24 hrs to obtain 1.29 g of a palladium catalyst supported on a silica-based carrier (palladium particle average-size: 5 nm, palladium content: 0.78%, palladium yield: 94.5%).

Figure 2:
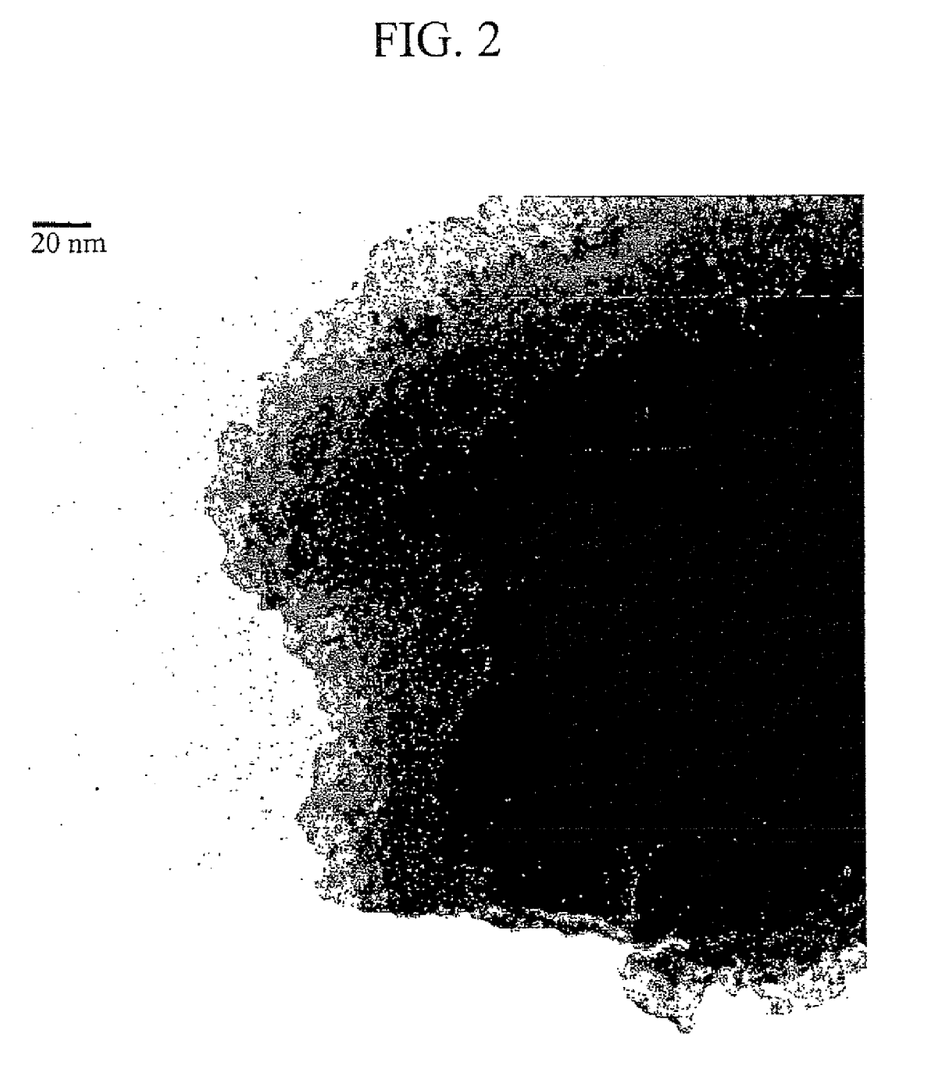
FIGS. 2 and 3: TEM photographs of the palladium catalysts prepared in Examples 2 and 3, respectively.

A TEM photograph of the supported palladium catalyst thus obtained is shown in FIG. 2.

EXAMPLE 3

0.42 g (2.20 mmol) of tertraethylene glycol, 0.25 g (0.22 mmol) of tetrakistriphenylphosphine palladium(0) and 10.9 g (38.5 mmol) of titanium tetraisopropoxide were mixed in a 25 mL reaction vessel and kept at 120° C. for 2 hours. Then, 1.80 mL of water was added thereto, the mixture was kept at the same temperature for 10 hours, and then cooled to room temperature. The precipitated solids were filtered, washed three times with 10 mL of acetone and dried for 24 hrs to obtain 3.95 g of a palladium catalyst supported on a titania-based carrier palladium particle average-size: 5 nm n, palladium content: 0.59%, palladium yield: 97.4%).

Figure 3:
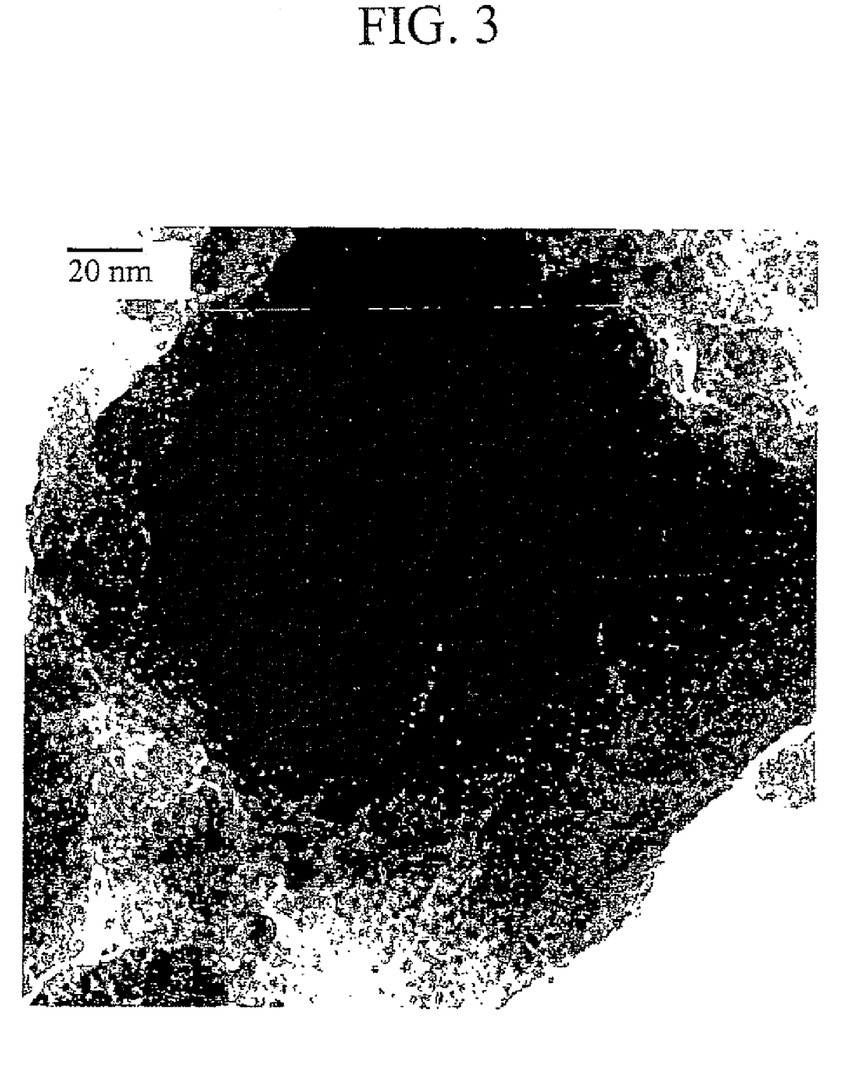

A TEM photograph of the supported palladium catalyst thus obtained is shown in FIG. 3.

<Performance of Various Organic Reactions Using Inventive Palladium Catalysts>

EXAMPLE 4

0.180 g (1.0 mmol) of trans-stilbene, a measured amount of the supported palladium catalyst prepared in Example 3 (the amount corresponding to 2 mol % of palladium based on the amount of trans-stilbene) and 4 mL of ethylacetate were mixed and stirred at room temperature for 60 min under 1 atm of $H_2$. The resulting mixture was filtered and the solvent was removed. The resulting residue was subject to silica gel column chromatography (eluent: hexane/ethylacetate(10/1)) to obtain 0.182 g of the title compound, 1,2-diphenylethane (yield: 100%).

The supported palladium catalyst used in the above reaction was simply recovered by filtration, and it retained its original activity even after 15 recycles.

EXAMPLES 5 TO 14

The procedure of Example 4 was repeated employing the specifics shown in Table 1, to perform the hydrogenation of various alkynes or alkenes, whose respective yields are listed in Table 1.

TABLE 1

| Ex. | Substrates | Products | Time (h) | Yield (%) |
|---|---|---|---|---|
| 5 | MeO$_2$C━━━CO$_2$Me | MeO$_2$C⁀⁀CO$_2$Me | 1 | 100 |

TABLE 1-continued

| Ex. | Substrates | Products | Time (h) | Yield (%) |
|---|---|---|---|---|
| 6 | Ph—≡—Ph | Ph-CH2-CH2-Ph | 1 | 100 |
| 7 | Ph-CH=CH-CH=CH-Ph | Ph-(CH2)4-Ph | 1 | 100 |
| 8 | Ph-CH=CH-C(O)-CH3 | Ph-CH2-CH2-C(O)-CH3 | 1 | 99 |
| 9 | Ph-CH=CH-C(O)-OMe | Ph-CH2-CH2-C(O)-OMe | 1 | 100 |
| 10 | Ph-CH=CH-C(O)-OH | Ph-CH2-CH2-C(O)-OH | 1 | 100 |
| 11 | 3-methylcyclohex-2-enone | 3-methylcyclohexanone | 12 | 100 |
| 12 | 5-methylfuran-2(5H)-one | 5-methyldihydrofuran-2(3H)-one | 12 | 100 |
| 13 | Oleic acid | Octadecanoic acid | 12 | 100 |
| 14 | Cholesterol | Cholestane | 24 | 16 |

EXAMPLE 15

0.122 g (1.0 mmol) of phenylethylalcohol, a measured amount of the supported palladium catalyst prepared in Example 1 (the amount corresponding to 0.5 mol % of palladium based on the amount of phenylethylalcohol) and 2 mL of toluene were mixed and refluxed for 6 hrs under 1 atmospheric air pressure. The resulting mixture was filtered and the solvent was removed. The resulting residue was subject to silica gel column chromatography (eluent: hexane/ethylacetate(5/1)) to obtain 0.120 g of the title compound, acetophenone (yield: 99%).

The supported palladium catalyst used in the above reaction was simply recovered by filtration, and it retained its original activity even after 15 recycles.

In contrast to the above, the procedure of Example 15 was repeated using commercially available 5% Pd/Al₂O₃ in an amount which was equivalent to the amount of palladium used in the above reaction, to obtain acetophenone in a low yield of only 31%.

EXAMPLES 16 TO 26

The procedure of Example 15 was repeated employing the substrates shown in Table 2 in a mixed solvent of trifluorotoluene (TFT) and toluene, to perform oxidations of various alcohols or diols, i.e., the conversion of corresponding esters or aldehydes. The observed yields are listed in Table 2 (the values in parentheses belong to cases of employing toluene as the solvent).

TABLE 2

| Ex. | Substrates | Products | Catalyst mol % | Temp. (°C.) | Time (h) | Yield (%) |
|---|---|---|---|---|---|---|
| 16 | 1-(4-methoxyphenyl)ethanol | 4'-methoxyacetophenone | 0.20 (0.50) | 80 (80) | 1 (6) | >99 (>99) |
| 17 | 1-(4-chlorophenyl)ethanol | 4'-chloroacetophenone | 2.0 (2.0) | 100 (110) | 24 (45) | 88 (87) |
| 18 | 1-indanol | 1-indanone | 0.20 (0.50) | 80 (80) | 3 (6) | >99 (>99) |
| 19 | 2-octanol | 2-octanone | 1.0 (2.0) | 100 (110) | 4 (20) | >99 (81) |
| 20 | 1-cyclohexylethanol | 1-cyclohexylethanone | 1.0 (2.0) | 100 (110) | 10 (18) | 94 (86) |
| 21 | benzyl alcohol | benzaldehyde | (0.50) | (70) | (2) | (>99) |
| 22 | 1,2-benzenedimethanol | phthalide | (0.50) | (80) | (12) | (99[d]) |
| 23 | 1,4-butanediol | γ-butyrolactone | (2.0) | (110) | (16) | (99[d]) |
| 24 | 1-octanol | octanal | 2.0 (2.0) | 100 (110) | 12 (12) | 19 (<5) |
| 25 | 1-(pyridin-4-yl)ethanol | 4-acetylpyridine | 5.0 (1.0) | 100 (110) | 14 (12) | 92 (62) |
| 26 | 2-thiophenemethanol | 2-thiophenecarboxaldehyde | 5.0 (1.0) | 100 (110) | 18 (24) | 90 (64) |

EXAMPLE 27

The oxidation of cholesterol in accordance with the above scheme was conducted by a procedure similar to that used in Example 15 (yield: 99%).

EXAMPLE 28

0.262 g (1.0 mmol) of methyl 4-iodobenzoate, 0.424 g (2.0 mmol) of potassium phosphate, 0.461 g (2.2 mmol) of phenyl boronic acid, a measured amount of the supported palladium catalyst prepared in Example 3 (the amount corresponding to 0.75 mol % of palladium based on the amount of methyl 4-iodobenzoate) and 3 mL of toluene were mixed and stirred at 110° C. for 5 hrs under an argon atmosphere. The resulting mixture was filtered and the solvent was removed. The resulting residue was subject to silica gel column chromatography (eluent: hexane/ethylacetate(8/1)) to obtain 0.213 g of the title compound, methyl biphenyl-4-carboxylic ester (yield: 100%).

The supported palladium catalyst used in the above reaction was simply recovered by filtration, and it retained its original activity even after 3 recycles.

EXAMPLE 29

49.4 mmol of cyclohexene, and a measured amount of each of the supported palladium catalyst prepared in Examples 1 and 3, commercially available 5% Pd/C and 5% Pd/Al$_2$O$_3$ (the amount corresponding to 0.83 mol % of palladium based on the amount of cyclohexene) were mixed and stirred at 40° C. for 24 hrs under 1 atm of H$_2$. The resulting mixture was filtered and the solvent was removed. The resulting residue was subject to silica gel column chromatography (eluent: hexane/ethylacetate(8/1)) to obtain the title compound, cyclohexane.

The yields of cyclohexane thus obtained are listed in Table 3.

TABLE 3

| Catalyst | Yield (%) |
| --- | --- |
| Example 1 | >99 |
| Example 3 | 30 |
| 5% Pd/C | 11 |
| 5% Pd/Al$_2$O$_3$ | 7 |

As described above, in accordance with the method of the present invention, a recyclable supported transition metal catalyst which has a high activity and keeps its original activity even after repeated use of more than 15 recycles can be easily synthesized in one pot. The inventive catalyst can be advantageously employed in the hydrogenation of alkenes and alkynes, the oxidation of alcohols, carbon-carbon coupling reactions and the like.

While the invention has been described with respect to the above specific embodiments, it should be recognized that various modifications and changes may be made to the invention by those skilled in the art which also fall within the scope of the invention as defined by the appended claims.

What is claimed is:

1. A method for preparing a supported transition metal catalyst, which comprises mixing with heating an organic transition metal complex, a metal-chelating agent and an alkoxide of a metal selected from the group consisting of Ti, Al and Si, and adding water thereto to induce a sol-gel reaction.

2. The method of claim 1, wherein the organic transition metal complex comprises at least one transition metal selected from the group consisting of Pd, Pt, Ru, Ni, Ir, Co, Rh, Os, Sm, Fe, Sc, Se, Re, Au and Ag.

3. The method of claim 2, wherein the organic transition metal complex comprises Pd.

4. The method of claim 1, wherein the organic transition metal complex comprises at least one ligand selected from the group consisting of hydride, chloride, cyanide, acetyl, triphenylphosphine, dibenzylidene acetone, carbonyl and diene.

5. The method of claim 1, wherein the organic transition metal complex is selected from the group consisting of tetrakistriphenylphosphine palladium(0), palladium(II) acetate, palladium(II) chloride, trisdibenzylidene acetone dipalladium(0), trisdibenzylidene acetone dipalladium(0) chloroform adduct, bis[1,2-bis(diphenylphosphino)ethane] palladium(0), bis(tri-t-butylphosphino)palladium(0), bis(tricyclohexylphosphino)palladium(0) and a mixture thereof.

6. The method of claim 1, wherein the metal-chelating agent is a polyethylene glycol having 1 to 30 ethylene repeating units or an alcohol having 1 to 10 carbon atoms.

7. The method of claim 1, wherein the metal-chelating agent is employed in an amount ranging from 1 to 500 mol based on 1 mol of the transition metal complex.

8. The method of claim 1, wherein the metal alkoxide is selected from the group consisting of tetraalkyl orthosilicate ($Si(OR)_4$), titanium(IV) tetraalkoxide ($Ti(OR)_4$), aluminum (III) trialkoxide ($Al(OR)_3$) and a mixture thereof, R being $CO_{1-4}$ alkyl.

9. The method of claim 1, wherein the metal alkoxide is employed in an amount ranging from 10 to 1000 mol based on 1 mol of the transition metal complex.

10. The method of claim 1, wherein the mixing of starting materials is conducted at a temperature ranging from 50 to 200° C. for 2 to 20 hrs.

11. The method of claim 1, wherein the water is employed in an amount ranging from 1 to 100 mol based on 1 mol of the metal alkoxide.

12. The method of claim 1, wherein the sol-gel reaction is conducted at a temperature ranging from 50 to 200° C. for 1 to 20 hrs.

13. A supported transition metal catalyst prepared by any one of the methods of claims 1 to 12.

* * * * *